(12) United States Patent
Galley

(10) Patent No.: US 9,895,166 B2
(45) Date of Patent: Feb. 20, 2018

(54) VARIABLE FLOW SMOKE EVACUATION APPARATUS

(71) Applicant: LAPROSURGE LTD., Hertfordshire (GB)

(72) Inventor: Geoffrey Galley, Hertfordshire (GB)

(73) Assignee: Laprosurge Ltd., Hertfordshire (GB)

( * ) Notice: Subject to any disclaimer, the term of this patent is extended or adjusted under 35 U.S.C. 154(b) by 0 days.

(21) Appl. No.: 15/300,149

(22) PCT Filed: Mar. 31, 2015

(86) PCT No.: PCT/GB2015/050986
§ 371 (c)(1),
(2) Date: Sep. 28, 2016

(87) PCT Pub. No.: WO2015/150783
PCT Pub. Date: Oct. 8, 2015

(65) Prior Publication Data
US 2017/0181768 A1    Jun. 29, 2017

(30) Foreign Application Priority Data
Mar. 31, 2014   (GB) .................................. 1405807.7

(51) Int. Cl.
*A61B 1/015*    (2006.01)
*A61M 1/00*     (2006.01)
(Continued)

(52) U.S. Cl.
CPC .... *A61B 17/3474* (2013.01); *A61B 2218/007* (2013.01); *A61B 2218/008* (2013.01)

(58) Field of Classification Search
CPC .......... A61B 17/3474; A61B 2218/007; A61B 2218/008; A61B 2217/005; B01D 27/108;
(Continued)

(56) References Cited

U.S. PATENT DOCUMENTS 2,834,520 A * 5/1958 Nyden ................. B65D 47/247
                                                      222/525
2,895,613 A * 7/1959 Griffiths ............... B01D 29/055
                                                      210/130
(Continued)

FOREIGN PATENT DOCUMENTS

EP          2305157 A1    4/2011
GB          2471650 A     1/2011
(Continued)

OTHER PUBLICATIONS

Search Report received in Great Britain Application No. 1405807.7 dated Oct. 15, 2014.
(Continued)

*Primary Examiner* — Adam Marcetich
(74) *Attorney, Agent, or Firm* — Ajay A. Jagtiani; Miles & Stockbridge P.C.

(57) ABSTRACT

The invention resides in a filter apparatus configured for use in the evacuation of smoke and other contaminants from a laparosurgical operating site incorporating an integral variable flow control mechanism. The apparatus can have a housing having an inlet and an outlet, and configured to allow fluid communication between the inlet and outlet, and a filter component arranged between the inlet and the outlet for filtering surgical smoke. A structure is provided having an aperture for providing a channel for fluid flow between the inlet and outlet. A closure is also provided and is configured to releasably engage with the structure. The housing is configured to be movable, in relation to the closure or the structure, between (i) a first position in which there is fluid communication between and through the channel and (ii) a second position in which the structure and the closure engage to inhibit fluid flow through the housing.

22 Claims, 2 Drawing Sheets

(51) Int. Cl.
*A61M 39/10* (2006.01)
*A61B 17/34* (2006.01)

(58) Field of Classification Search
CPC . F16K 1/422; F16K 1/42; F16K 31/50; F16K 31/504; F16K 31/506; F16K 31/508; F16K 1/123; F16K 31/1228; A61J 15/0092; A61J 1/2037; A61J 1/2031; A61J 1/2051; A61J 11/002; A61M 13/003; A61M 13/006; A61M 1/0052
See application file for complete search history.

(56) References Cited

U.S. PATENT DOCUMENTS

| | | | | |
|---|---|---|---|---|
| 2,936,935 A * | 5/1960 | Rabb | ............... | B65D 47/247 222/525 |
| 3,756,273 A * | 9/1973 | Hengesbach | ......... | F16K 15/026 137/540 |
| 4,489,914 A * | 12/1984 | Stevenson | ............... | B05B 1/304 239/579 |
| 4,696,411 A * | 9/1987 | Graf | .................. | B01J 4/001 141/326 |
| 4,735,603 A | 4/1988 | Goodson et al. | | |
| 4,976,404 A * | 12/1990 | Ichikawa | ............... | F16K 47/04 251/121 |
| 5,197,634 A * | 3/1993 | Beck | ................... | B65D 47/243 222/109 |
| 5,514,087 A | 5/1996 | Jones | | |
| 5,578,000 A | 11/1996 | Greff et al. | | |
| 5,688,256 A * | 11/1997 | Surratt | ............... | A61M 1/0052 604/19 |
| 5,709,675 A | 1/1998 | Williams | | |
| 5,722,962 A | 3/1998 | Garcia | | |
| 5,968,032 A | 10/1999 | Sleister | | |
| 6,299,027 B1 * | 10/2001 | Berge | ................... | B65D 47/248 222/153.14 |
| 6,592,543 B1 | 7/2003 | Wortrich et al. | | |
| 2003/0183662 A1 * | 10/2003 | Ingram | ............... | B65D 47/263 222/548 |
| 2003/0226860 A1 * | 12/2003 | Godwin | ............... | B65D 47/263 222/568 |
| 2004/0144792 A1 * | 7/2004 | Næsje | ................ | A47G 19/2272 220/714 |
| 2004/0149785 A1 * | 8/2004 | Fracasso | ............... | B65D 47/243 222/525 |
| 2005/0218165 A1 * | 10/2005 | Yang | ................... | B65D 47/283 222/526 |
| 2008/0011971 A1 * | 1/2008 | Stoll | ...................... | F16K 24/04 251/89 |
| 2008/0308183 A1 * | 12/2008 | Law | ....................... | B65D 41/26 141/380 |
| 2011/0068134 A1 * | 3/2011 | Yang | .................. | B65D 47/242 222/519 |
| 2014/0165842 A1 * | 6/2014 | Bonano | ................ | A61M 5/165 96/142 |

FOREIGN PATENT DOCUMENTS

| | | |
|---|---|---|
| WO | 93/25248 A1 | 12/1993 |
| WO | 99/31954 A2 | 7/1999 |
| WO | 2007/038538 A1 | 4/2007 |

OTHER PUBLICATIONS

International Search Report and Written Opinion received in PCT Application No. PCT/GB2015/050986 dated May 28, 2015.

* cited by examiner

VARIABLE FLOW SMOKE EVACUATION APPARATUS

The invention relates to an apparatus for smoke evacuation and in particular a variable flow apparatus including a filter for the removal of gases and/or solids from a body during a laparoscopic surgical procedure.

During a laparoscopic procedure it is important to maintain the required degree of pressure within the body cavity which is subject to leakages of the insufflating gas around inserted instruments and devices known as trocars and cannulas which are entered into the abdominal cavity to achieve insufflation of the cavity and to give access for surgical instruments to the operating site within the cavity. Pressure is generally maintained within the cavity either by a continuous flow of $CO_2$ into the cavity through the insufflating port which compensates for the loss of pressure through leakages or through periodic bursts of insufflation which restore pressure to a predetermined level. Current laparosurgery systems are equipped with sensors which continually monitor the pressure and provide the required degree of insufflation as soon as the pressure drops below a predetermined level.

An important requirement of the laparosurgical procedure is that of removing smoke particulates, vapours and other materials produced during the act of laser ablation or cauterisation of tissue within the cavity. Such contaminants obscure the field of view of the surgeon and it is essential that they are evacuated in a short period of time in order to avoid delay and interference with the surgical procedure.

The clearance of said contaminants requires a significant flow of $CO_2$ gas through the cavity which exits the cavity through a provided exhaust trocar or cannula where after the exhausted gas and contaminants may be passed through a filtration means and exhausted into the ambient air of operating theatre.

As will be seen in the following descriptions of prior art, systems have been provided which filter the contaminants from the gas within the cavity without additional flow of gas through the cavity (see U.S. Pat. No. 5,709,675), re-enter the exhausted gas into the cavity after filtration (see U.S. Pat. No. 4,735,603) or which dispose of the exhausted gas without filtration into an operating theatre wall vacuum (see U.S. Pat. No. 5,578,000). However, the practice in general use at the present time is that of creating additional gas flow through the cavity, filtering (and deodorising) the exhausted gas and allowing the filtered and deodorised exhaust to enter the ambient air of the operating theatre.

U.S. Pat. No. 4,735,603 (Goodson et al) appears to disclose a smoke evacuating system for use during surgical procedures, particularly minimally invasive procedures involving the use of a laser or cauterizing instrument at a surgical site having an associated higher than ambient pressure, wherein the system includes a filter with a site side and an outlet side and a fluid conduit extending between the surgical site and the filter. The filter exhibits low resistance or a low pressure drop and resists fluid flow, whereby the higher than ambient pressure is not substantially diminished and generates a fluid flow in the fluid flow path tending to carry smoke to and through the filter. This system enables a continuous input of $CO_2$ at a relatively low flow rate sufficient to maintain the required degree of pressure in the operating cavity and to compensate for leakage of the gas from the various trocar entry sites. The removal of smoke and other contaminants from the operating site is achieved by passage of the exhaust gas emerging from an exhaust trocar through a filter before returning it to the input trocar. This system being capable of only limited flow rates of the exhaust gas through the filter suffers from slow clearance of smoke from the operating sites which limits the work rate of the surgeon while waiting for clearance of the visual field.

U.S. Pat. No. 5,578,000 (Greff) appears to disclose a laparoscopic smoke evacuation system for removing surgical smoke containing undesirable contaminants, including a trocar having a working channel adapted to provide access to an operative site and a stopcock communicating with the working channel. A source of vacuum is coupled through a fluid conduit to the stopcock to remove the smoke. Filtration is provided along the fluid conduit to remove the undesirable contaminants and the residual gas is exhausted to the room or the source of vacuum. A liquid collector can also be disposed along the fluid conduit together with valve means which is either mechanically or electrically operable to control application of suction to the trocar. While this patent relies on a powerful wall vacuum source usually available in an operating theatre or alternatively a mobile vacuum system with inbuilt filtration, problems continue to arise from imbalances created when the smoke clearing vacuum is applied to the operating cavity as the gas exhausting to the room or to a wall source must be replenished by the $CO_2$ input and if a rapid clearance is required a substantial flow rate of gas will be established through the operating cavity with the attendant problem of cooling and drying of tissue within the body cavity.

U.S. Pat. No. 5,722,962 (Garcia) appears to describe a trocar assembly for exhausting gas from a body cavity comprising a trocar having a housing with a flow passage therethrough which terminates in an outlet fitting, and a filter mounted thereon. The filter includes a housing with a chamber, and an inlet and an outlet which communicate with opposite sides of the chamber to provide a flow passage therethrough. About the inlet is a fitting and there is a means on the inlet fitting of mounting the filter on the outlet fitting of the trocar housing. Within the chamber is a filter means so that effluent gas passing through the trocar flows through the filter means prior to exiting through the outlet of the filter. This system relies on the high ambient pressure in the operating cavity to provide flow through the filter component when it is desired to remove smoke from the cavity the said exhausted gas is made up by a further input of gas through the insufflating trocar. Thus the flow rate of exhaust gas is limited by the extent to which the pressure in the operating cavity may be reduced before the cavity begins to collapse and the re-insufflation makes up the loss. If the re-insufflation is automatically switched on as pressure in the cavity begins to drop, which is the case in known laparosurgical operating systems, the rate of exhaust flow will either be constant due to the selection of a particular filter or a means of controlling the exhaust flow such as a ratchet clamp or a stopcock must be provided at some point along the conduit which must be opened to the extent required to create the required increased exhaust flow rate. The adjustment of flow rates using flow limiting devices such as stop cocks or ratchet clamps is unsatisfactory as the said stop cocks or ratchet clamps are not intended for the controlled reduction or increase of flow required for relatively short periods of smoke and contaminant clearing described.

U.S. Pat. No. 5,709,675 (Williams) appears to disclose a smoke reducing device for use in minimally invasive surgery including a housing having an inlet opening from an outlet opening. The housing is sized to fit through a trocar opening that leads to a body cavity. A filter is positioned within the housing between the inlet and outlet openings. An air flow generator is located within the housing and is positioned to draw air in through the inlet opening, pulled through the filter, and exhausted through the outlet opening to draw any smoke created during minimally invasive surgery through the filter. The smoke reducing device may form part of an electrocautery device such that smoke created during minimally invasive surgery can be filtered internally within the body cavity. In this case the smoke evacuating device is independent of the insufflation system having its own gas input and extraction after passing through an internal filter. As the input and extraction ports are contained within the body cavity the device is effectively circulating gas that is contained within the body cavity through its internal disposable filtration system and therefore has no impact on the flow rates and pressures developed by the insufflation system. It appears from the dimensions of the device that it is unlikely to provide a flow rate between the input and exhaust ports sufficient to achieve an acceptable rate of smoke extraction which will provide for the surgeon a rapid clearance of smoke and vapours so as to permit minimal delays in the surgical procedure.

EP1039961 (Drogue) appears to describe a smoke evacuating system for use during surgical procedures, particularly minimally invasive procedures involving the use of a laser or a cauterisation device at a surgical site having an associated higher than ambient pressure, wherein the system includes a filter with a site side and an outlet side and a fluid conduit extending between the surgical site and the filter. The filter exhibits low resistance or a low pressure drop and resists fluid flow, whereby the higher than ambient pressure is not substantially diminished and generates a fluid flow in the fluid flow path tending to carry smoke to and through the filter. This patent has in common with all other patents discussed herein the passage of gas contaminated with smoke, vapour and other impurities which result from laparoscopic laser and or cauterizing surgical procedures, through a filter in order to remove said impurities before exhausting the cleaned gas either into the said body cavity or the operating theatre environment or into a vacuum extraction system. It again appears to exhibit the defect of a stable flow rate which is insufficient to provide rapid clearance of smoke and other impurities required during laparosurgical procedures.

Few details of the filter construction such as size and porosity are included in any of the above patents as the filters used in connection with laparoscopic surgical procedures are freely available and well known to those skilled in the art. In any event the flow rate through any filter and the resulting pressure drop across the said filter is determined by a group of parameters including the porosity of the filter materials, the cross sectional area and thickness of the filter membrane (s) and the pressure and flow rate of gas which is presented at the filter inlet port.

In addition, as the available flow rates have increased significantly since the beginning of the laparosurgical art, means such as stop cocks or ratchet clamps are generally employed to allow increased flow rates at particular times during the operative procedure in order to allow a rapid clearance of smoke and vapours which may be obstructing the visual field of the surgeon immediately following a period of laser or cauterizing activity. The adjustment of flow rates using flow limiting devices such as stop cocks or ratchet clamps is unsatisfactory as these devices are not intended for the controlled reduction or increase of flow required for relatively short periods of evacuation of smoke and other impurities.

An example of the development of the laparosurgical art in particular relation to increased insufflation pressures and flow rates is evident in U.S. Pat. No. 6,592,543. This patent describes a fluid flow regulator of a smoke evacuation system for use with laparoscopic and endoscopic surgery. The fluid flow regulator is comprised of a detachable diaphragm with one or more orifices of predetermined diameter to provide a significant obstruction to the flow of fluid through the evacuation system. When operatively coupled to the pressurized surgical site, the fluid flow regulator makes possible the continuous evacuation of surgical smoke while simultaneously maintaining the pneumoperitoneum in a distended position for the duration of the laparoscopic procedure.

The inventors have considered the known smoke/vapour/odour removal filters as mentioned in the above referenced prior art and, in particular, EP1039961, which may be placed in the conduit of exhaust gas from the operating cavity in order to remove smoke, vapours, odours and other impurities. Said smoke removal filter did not in practice provide a sufficient resistance to limit continuous flow exhaust from a surgical site to an acceptable value given the level of insufflation pressure maintained in the operating cavity. The inventors subsequently modified EP1039961 to introduce a simple flow restriction member, or diaphragm, to the exhaust port of the filter thereby achieving a fixed flow rate lower than that provided by the filter alone and acceptable in general use to provide such rate as had been previously disclosed. However, the reduced but constant rate proved inadequate regulation in situations where a rapid clearance of smoke was required to provide the surgeon with improved visibility. Therefore, the diaphragm could be temporarily removed from the filter outlet port to allow a faster flow rate. This removal and replacement of a small diaphragm is clearly an inadequate and poorly controlled method of regulating flow during an operating procedure.

The present invention aims to permit the exhaust gas originating from the operating cavity to flow through the exhaust filter at different flow rates depending on whether such exhaust gas results from a continuous background insufflation flow or whether it is the result of a short period of purging flow at higher flow volume which is required in order to provide rapid removal of smoke and other impurities from the visual field of the surgeon.

Accordingly the invention provides an apparatus comprised of one or more filter elements enclosed in a filter housing incorporating a novel variable flow control device, which can be quickly and conveniently used to produce a controlled increased flow rate and instantly returned to the predetermined background flow rate upon completion of the purging action. During the purging action pressure is maintained in the body cavity by automatic inflow of insufflating gas. A variable flow regulator can allow the adjustment of the flow rate of the gas passing through the said apparatus.

Accordingly, the invention generally resides in an apparatus configured for use in the evacuation of smoke and other contaminants from a laparosurgical operating site, wherein the filter has an integral variable flow control mechanism. The mechanism can be configured to be within the housing of the filter to inhibit any risk of contamination. The mechanism can be positioned upstream of the filter i.e. between the surgical site and the filter. The mechanism can be positioned upstream of the filter i.e. between the surgical site and the filter to enable the flow rate to be controlled before exhaust gas reaches the filter. Alternatively, the mechanism can be positioned downstream of the filter to inhibit fouling of the mechanism from contaminants.

According to one aspect, the invention resides in a smoke evacuation apparatus, the apparatus having: a housing having an inlet and an outlet, and configured to allow fluid communication between the inlet and outlet; a filter component arranged between the inlet and the outlet for filtering surgical smoke; a structure, having an aperture for providing a channel for fluid flow between the inlet and outlet; and a closure configured to releasably engage with the structure, wherein the housing is configured to be movable, in relation to the closure or the structure, between (i) a first position in which there is fluid communication between and through the channel and (ii) a second position in which the structure and the closure engage to inhibit fluid flow through the housing. The movement of the housing provides variable flow regulation.

The structure and the closure arrangement can be provided on the inlet side or the outlet side or on both the inlet and outlet side of the housing.

The structure can be a tubular component configured to threadedly engage with the inlet and/or outlet for connection to a flexible fluid conduit for connection to a surgical site, and the closure is arranged within the housing. The closure can be configured on a supporting element to enable fluid flow therearound in the first position.

The structure can be arranged within the housing and have a seat arranged around the aperture for engagement with the closure, which is configured as a plug and threadedly engages with the inlet. The closure can have an aperture configured to enable fluid flow between the inlet and the outlet in the first position.

A linear relationship can exists between the movement of the housing in relation to the closure or the structure and the size of the aperture. Alternatively, a non-linear relationship can be configured. The aperture can be substantially circular and the closure is preferably of a conical or curved conical cross section. The structure and closure can be configured to provide a flow limitation between the inlet and/or outlet and the filter.

According to another aspect, the invention can reside in an apparatus being a filter housing containing one or more filtration elements. Said filter housing is generally formed from two mating components which can be bonded or otherwise fitted together after positioning of filter elements in one of the said mating components. Said filter housing is provided with a tubular inlet and an integral outlet port, said ports configured to allow fluid communication between the inlet and outlet of the filter housing through the said filtration elements. The said tubular inlet port is inserted into the filter housing by means of a threaded section on said tubular inlet port which engages with a matching threaded section on the inlet side of the filter housing so that said tubular inlet port may be moved towards or away from the centre of said filter housing by rotation of said apparatus relative to said tubular input port. There is additionally provided within the inlet side of the filter housing a supporting structure which carries at its centre a solid form or "plug" capable of progressively closing the aperture of the tubular input port as the said input port is advanced by rotation of the apparatus relative to the said input port along the screwed section of the filter housing towards the centre of the filter housing. Conversely, rotation of the said apparatus in the opposite direction (away from the centre of the filter housing) will progressively open the said aperture of the said tubular input port. The aperture of the tubular input port is circular and the shape of the plug which progressively enters the aperture of the tubular input port is substantially conical.

According to the another aspect, the arrangement with associated threaded tubular port and integral port may be reversed so that the threaded tubular port engages with a threaded section on the outlet side of the filter housing and the integral port is on the input side of the filter housing which connects to a fluid conduit and thereby to the trocar which allows the exhaust gas to exit the operating site. In this case the supporting structure which carries at its centre the solid form or "plug" is located within the output side of the filter housing between the filter elements and the tubular output port and the movement of the tubular output port towards or away from the centre of the apparatus is achieved by rotation of the tubular output port which relative to the apparatus.

By arrangement of the pitch of the threads on the outside of the tubular port and the inside of the filter housing, the apparatus can be configured to provide a rapid closing of the aperture of the tubular input (or output) port with a minimal rotation of the tubular port relative to the apparatus or the closure may be more gradual requiring one or more full turns of the filter housing (or tubular port) to move from a fully open to a fully closed aperture.

Although the tubular port and housing have been described above having a threaded interface, the tubular port can additionally or alternatively be provided with a mechanism configured to enable sliding movement of the tubular port with respect to the housing. A linear movement can enable a rapid change in the flow rate. The linear movement can be substantially in the direction of the axis passing through the centre of the housing.

A mechanism configured to enable sliding movement of the tubular port with respect to the housing can be configured with stops or reference points such that a user has, for example, haptic feedback to indicate the extent of the linear movement. Two stops can be provided to indicate, for example, that the flow rate has been stopped (first position) and the flow rate is maximised (second position). A mechanism configured to enable sliding movement of the tubular port with respect to the housing can have lower production costs because the complexity of the tool manufacture is reduced. The mechanism can have a slide-rod and securing means, such as a cam, for releasably securing the position of tubular port with respect to the housing.

The tubular port and the filter housing may advantageously bear reference marks indicating the fully open, half open and fully closed positions of the aperture of the tubular port. Said tubular port and said filter housing may additionally be provided with limiting stops at the fully open and fully closed positions of the aperture of the tubular port facilitating rapid adjustment of the filter housing between fully closed and fully open conditions of the said aperture.

In order that the invention can be more readily understood, reference will now be made, by way of example, to the drawings in which:

FIG. 1 is cross-sectional view of a filter in accordance with the invention, while FIG. 1a is a detailed view of the inlet of FIG. 1 and FIG. 1b is a cross-section (II-II) through a portion of the filter shown in FIG. 1

FIG. 2 is cross-sectional view of another filter in accordance with the invention, while FIG. 2a is a detailed view of the inlet of FIG. 2 and FIG. 2b is a cross section (II-II) through a portion of the FIG. 2.

Figures 1, 1A, 1B:
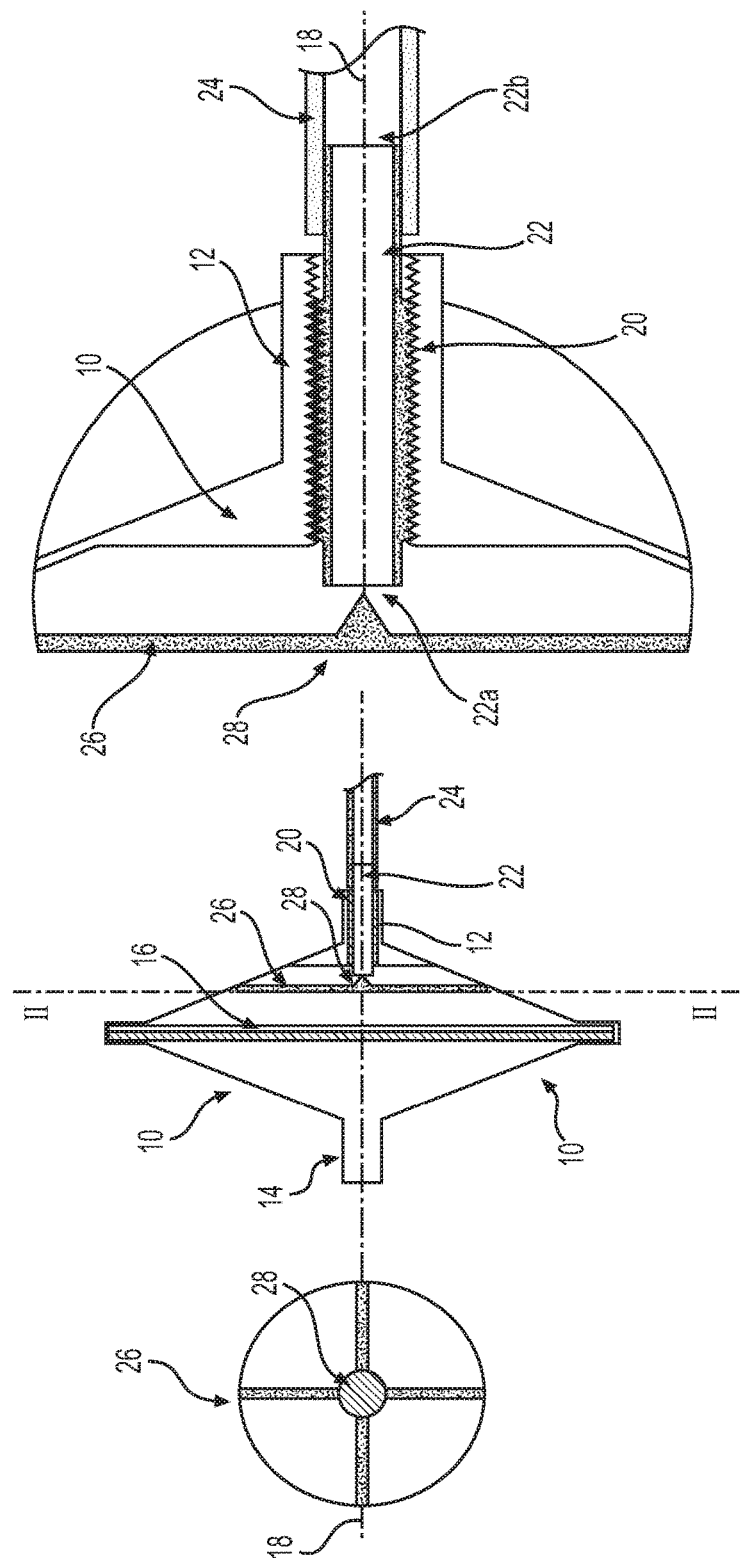

Referring to FIGS. 1, 1a, 1b and 2, 2a and 2b, the apparatus has a filter component having a housing 10 having an inlet 12 and an outlet 14. Arranged between the inlet and outlet is a filter 16 mounted in the housing. The filter can have one or more filter layers for removing smoke, odour and other contaminants from a fluid flow passing from the inlet to the outlet. The housing is substantially cylindrical with cone-shaped ends, which can be shallow in depth, with the inlet and outlet located at said ends. The inlet and outlet are arranged to define a substantially linear axis 18 extending through housing.

The inlet 12 is provided with a threaded portion 20 for receiving a corresponding threaded portion of a tubular structure 22. The tube has an aperture 22*a* within the housing 10 and an aperture 22*b* outside the housing.

The tube is configured to threadably engage with the inlet 12 of the housing 10. Movement, or rotation, of the tube with respect to the housing causes the tube to move in or out of the housing along the axis 18. The length of the tube is configured such that it can extend from inside the housing to outside the housing for connection to a flexible conduit 24. The flexible conduit 24 can be connected to a surgical site either via a trocar or cannula.

Within the housing 10, a supporting element 26 spans the interior of the housing 10 and is configured to support a closure member, or plug 28, within the space between the inlet 10 and the filter 16. By way of example four equally spaced arms extend from the side of the interior wall of the housing to support the plug. The plug is substantially cone-shaped and the central axis of the cone is aligned with the axis 18 of the housing. The supporting element and/or plug can be a separate component removably fitted to the housing.

Rotation of the tube 22 within the inlet 12 causes the tube to move in to or out of the housing 10. The plug 28 is configured such that the tube can be moved against the plug to close the aperture 22*a* of the tube thus inhibiting fluid flow from the inlet 12 to the outlet 14. The aperture can be configured with a seat for engaging with the plug.

In use, the flexible conduit 24 would be connected to a pressurised surgical site via, for example, a trocar. Gas and smoke flowing from the site would flow from the conduit and into the tube 22 and out of the aperture 22*a*. In an open position, fluid flows around the plug and past the supporting element 26 towards the filter. The cross-sectional form of the supporting elements 26 can be configured to minimise obstruction to the fluid flow. The fluid passes, at least in part, through the filter 16 and exits the housing 10 via the outlet 14.

The position of the plug 28 in relation to the aperture 22*a* determines the flow rate around the plug. Rotation of the housing 10 in one direction with respect to the tube 22 causes the tube to move into the housing and towards the plug 28. As the aperture 22*a* at the end of the tube approaches and moves over the plug the fluid flow becomes restricted. Restriction of the fluid flow increases until the plug effectively closes the aperture 22*a* thus preventing fluid flow into the housing 10.

There can be a linear relationship between the rotation of the housing 10 with respect to the tube 22. Alternatively, the plug can be shaped such that there is a non-linear relationship between rotation and flow regulation. A non-linear relationship can be provided across a range of movement to enable a rapid change in the flow rate e.g. for rapid shut-off capability.

By way of example, a surgeon looking to adjust the pressure within the surgical site can adjust the apparatus of the invention to increase or decrease the fluid flow from the site. To do so, the surgeon would take hold of the fluid conduit 10 in one hand and rotate the filter housing relative to the fluid conduit with the other hand. Rotation of the housing 10 in a clockwise direction relative to the fluid conduit moves the tube 22 closer to the plug 28 while an anticlockwise rotation moves the plug 28 further away from the tube 22.

The filter can be provided with a support means, such as a stand, that improves the ergonomic handling of the filter to facilitate rotation of the housing 10 with respect to the tube 24. This improves the operation of the filter and adjustment of flow regulation during surgery. By way of example, when a surgeon requires a short period of rapidly increased flow in order to clear the visual field inside the operating cavity, the surgeon, or more likely a theatre assistant, can rotate the filter housing relative to the inlet port so as to increase the flow until clarity of the surgeons visual field is achieved at which point the filter housing or can be returned to its original position. During the period of increased flow the pressure within the operating cavity is maintained at a predetermined level by automatic operation of the insufflations system controlled by a pressure sensor located in the flow path of the $CO_2$ into the operating cavity.

Integrally moulded stops can limit the movement of the tube 22 to inhibit damage to the plug 28 and support element 26, or inhibit detachment of the housing from the tube. Additionally or alternatively, indentations or mechanical indicators can be configured to provide haptic and/or audible feedback on the position of the tube with respect to the plug. By way of example, each 90-degree rotation would result in an audible 'click' sound indicating that the flow rate had changed by 10%.

Overall, the apparatus provides a filter housing with suitable filter elements and an integral variable flow adjustment system. This permits precise adjustment of flow by means of an obstruction element (plug) positioned concentrically with the flow inlet at the aperture 22*a*. The threaded portion 20 of the filter housing facilitates smooth controllable movement of the tube 22.

The housing and/or tube 22 can be marked with indications such that the relative flow-rate can be read for a given position.

In an alternative configuration, the flexible conduit 24 can be connected to the housing 10 via a fixed inlet conduit and the tube 22, supporting element 26 and the plug 28 are arranged on the outlet side of system. To be clear, the plug is arranged between the filter and the outlet 14.

The structural features, operation and function of the components operation is the same as described above except that, in use, the flexible conduit 24 would be connected to a pressurised surgical site via, for example, a trocar. Gas and smoke flowing from the site would flow from the hose through the outlet and, at least in part, through the filter 16.

In an open position, fluid flows around the plug 28 and past the supporting element 26 towards the tube 22, which is threadably arranged on the outlet 14, and out of the apparatus.

The position of the plug 28 in relation to the aperture 22*a* of the tube 22 determines the flow rate around the plug in the same way as described for FIG. 1. In the embodiment, the tube can be rotated with respect to the housing such that the tube 22 moves into the housing and towards the plug 28. As the aperture 22*a* at the end of the tube approaches and moves over the plug the fluid flow becomes restricted. Restriction of the fluid flow increases until the plug effectively closes the aperture 22*a* thus preventing fluid flow into the housing 10.

Figures 2, 2A, 2B:
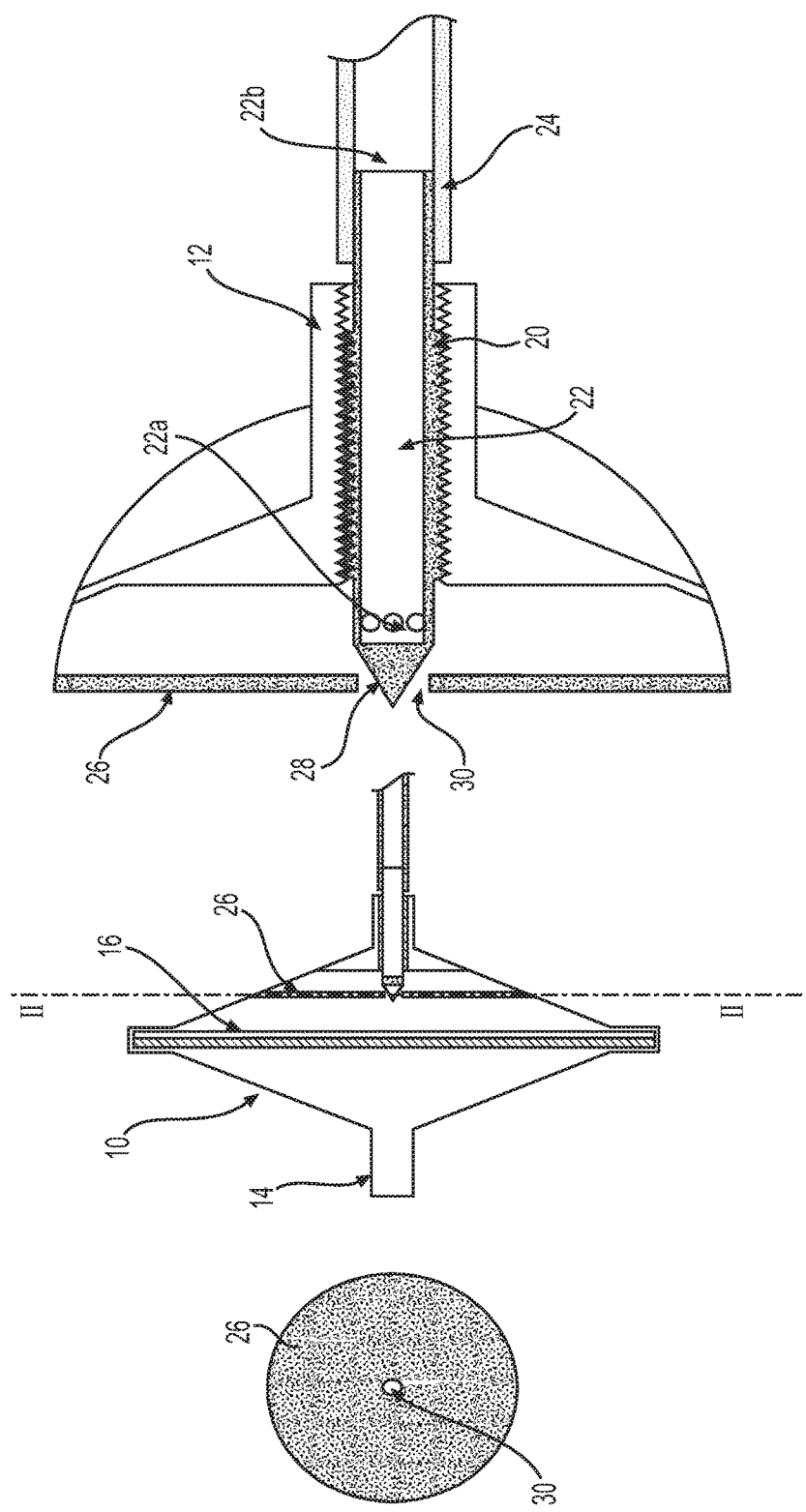

FIG. 2 shows another configuration of the invention. Like features are described using like numerals. The filter apparatus has a filter component 8 having a housing 10, inlet 12, outlet 14 and filter 16, as per the arrangement of FIG. 1.

The inlet 12 is provided with a threaded portion 20 for receiving a corresponding threaded portion of a tubular component 22. The tubular component has an aperture 22a within the housing 10 and an aperture 22b outside the housing. The end of the tube located within the housing 10 is closed. Said end is substantially cone-shaped.

The tube is configured to threadably engage with the inlet 12 of the housing 10. Movement, or rotation, of the housing with respect to the tube causes the tube to move in or out of the housing. The length of the tube is configured such that it can extend from inside the housing to outside the housing for connection to a tubular conduit 24. The tubular conduit 24 can be connected to a surgical site via a trocar or a cannula.

In a similar manner to FIG. 1, the cone-shaped plug 28, now located on the end of the tube 22, is aligned with the axis 18 of the housing.

Within the housing 10, a supporting element 26 spans the interior of the housing 10 and is configured to provide a port 30 between the inlet 12 and the filter 16. The support 26 forms a barrier to restrict fluid flow from the inlet to the filter to pass through the port 30.

Rotation of the tube 22 within the inlet 12 causes the tube to move in to or out of the housing 10. The tube 22 is configured such that the plug 28 which is now formed by the end closure of the tubular member 22 can be moved into the port 30 to close the port thus inhibiting fluid flow from the inlet 12 to the outlet 14. The port 30 can be provided with a seat to engage with the plug.

In use, the filter is configured in the same manner as per FIG. 1. In an open position, fluid flows through the tube 22 and out of the aperture 22a and around the plug 28 and through the port 30 towards the filter. The fluid passes, at least in part, through the filter 16 and exits the housing 10 via the outlet 14.

The position of the plug 28 in relation to the port 30 determines the flow rate around the plug. Rotation of the housing 10 in one direction with respect to the tube 22 causes the tube to move into the housing such that the plug 28 at the end of the tube approaches the port the fluid flow becomes restricted. Restriction of the fluid flow increases until the plug effectively closes the port thus preventing fluid flow into the housing 10.

The function of the plug 28 and aperture 22a of FIG. 1 is analogous to the plug 28 and port 30 of FIG. 3 and, therefore, the teaching associated with FIG. 1 similarly applies to FIG. 2.

The apparatus can also be configured for applications in which the regulation of flow control is required when filtering liquids.

The present invention has been described above purely by way of example, and modifications can be made within the spirit and scope of the invention, which extends to equivalents of the features described and combinations of one or more features described herein. The invention also consists in any individual features described or implicit herein.

The invention claimed is:

1. A filter apparatus configured for use in the evacuation of smoke and other contaminants from a laparosurgical operating site incorporating an integral variable flow control mechanism, wherein said flow control mechanism is operable or controllable manually, the apparatus having:
a housing having an inlet and an outlet, and configured to allow fluid communication between the inlet and outlet;
a filter component arranged between the inlet and outlet for filtering surgical smoke;
a structure having a channel for fluid flow between the inlet and outlet;
a closure configured to releasably engage with the structure; and
a supporting element attached to the housing,
wherein the housing is configured to be rotatable in relation to the closure of the structure, between (i) a first position in which there is fluid communication between and through the channel and (ii) a second position in which the structure and the closure engage to inhibit fluid flow through the housing,
wherein the closure is disposed on the supporting element to enable fluid flow therearound in the first position.

2. An apparatus according to claim 1, wherein the structure is a tubular member configured to movably engage with the inlet and/or outlet for connection to a flexible tubular conduit configured for connection to a surgical site, and the closure is arranged within the housing.

3. An apparatus according to claim 2, wherein the tubular member is threaded.

4. An apparatus according to claim 1,
wherein the structure comprises an aperture,
wherein the structure is arranged within the housing and has a seat arranged around the aperture for engagement with the closure, which is configured as a plug and movably, engages with the inlet.

5. An apparatus according to claim 4, wherein the closure has an aperture configured to enable fluid flow between the inlet and the outlet in the first position.

6. An apparatus according to claim 1, wherein there is a linear relationship between the movement of the housing in relation to the closure or the structure and the size of the aperture.

7. An apparatus according to claim 1,
wherein the structure comprises an aperture,
wherein the aperture is substantially circular and the closure is substantially cone-shaped.

8. A smoke evacuation system, the system comprising:
a first component having an apparatus according to claim 1; and
a second component comprising: a housing having an inlet and an outlet, and configured to allow fluid communication between the inlet and outlet; and a filter component arranged between the inlet and the outlet for filtering surgical smoke,
wherein the first component and the second component are connected in series.

9. A filter apparatus configured for use in the evacuation of smoke and other contaminants from a laparosurgical operating site incorporating an integral variable flow control mechanism, wherein said flow control mechanism is operable or controllable manually, wherein the apparatus has:
a housing having an inlet and an outlet configured to allow fluid communication between the inlet and outlet;
one or more filtration elements arranged between the inlet and the outlet for filtering surgical smoke and other impurities emanating from a surgical site; and
a tubular input, or output, port having an aperture providing a channel for fluid flow between the inlet and outlet which is movably engaged with a tubular input, or output, member configured to move along the axis of the apparatus towards or away from the center of the filter apparatus; and
a closure in the form of a plug positioned on the axis of the filter apparatus and supported by a supporting element extending from an interior of the housing, said tubular input, or output, port engaging with the plug at a limit of its travel along the axis of the filter apparatus towards the center of the filter apparatus thereby inhibiting fluid flow between filter housing input and output, wherein movement of said tubular input, or output, member along the axis of the filter apparatus in a direction away from the center of the filter apparatus progressively opens the aperture of the tubular inlet or outlet port to point of maximum flow rate between the input and output of the filter apparatus.

10. An apparatus according to claim 9, wherein there is a linear relationship between the movement of the tubular input or output member in relation to the plug and the resulting cross sectional area of the aperture of the tubular input port.

11. An apparatus according to claim 9, wherein the aperture of the tubular input or output member is substantially circular and the closure is substantially cone-shaped.

12. An apparatus according to claim 9, wherein the tubular input or outlet member is threaded.

13. An apparatus according to claim 12, wherein the threaded tubular input or outlet member is closed at one end by a conical form and is provided with openings along an unthreaded section of the tubular input or output member to allow fluid flow into or out thereof.

14. An apparatus according to claim 13, wherein the supporting element comprises a baffle attached to the housing having a central aperture into which the conical form enters by movement of the tubular input or output member along an axis of the filter apparatus thereby progressively closing the central aperture of the baffle.

15. An apparatus according to claim 13, wherein the filter apparatus is configured for adjusting the movement of the closure relative to the aperture incrementally.

16. An apparatus according to claim 9, wherein the supporting element comprises two or more radial arms extending from an interior of the housing.

17. An apparatus according to claim 16, wherein the two or more radial arms form a cross-bar configuration.

18. A smoke evacuation kit, the kit having a filter apparatus: a kit;
wherein the filter apparatus is configured for use in the evacuation of smoke and other contaminants from a laparosurgical operating site incorporating an integral variable flow control mechanism, and
wherein said flow control mechanism is operable or controllable manually, the filter apparatus having:
a housing having an inlet and an outlet, and configured to allow fluid communication between the inlet and outlet;
a filter component arranged between the inlet and the outlet for filtering surgical smoke;
a structure having a channel for fluid flow between the inlet and outlet;
a closure configured to releasably engage with the structure; and
a supporting element attached to the housing,
wherein the housing is configured to be rotatable in relation to the closure of the structure, between (i) a first position in which there is fluid communication between and through the channel and (ii) a second position in which the structure and the closure engage to inhibit fluid flow through the housing,
wherein the closure is disposed on the supporting element to enable fluid flow therearound in the first position.

19. A filter apparatus comprising:
a housing having an inlet and an outlet, and configured to allow fluid communication between the inlet and outlet;
a filter component arranged between the inlet and the outlet;
a structure having a channel for fluid flow between the inlet and outlet;
a closure configured to releasably engage with the structure; and
a supporting element attached to the housing,
wherein the housing is configured to be rotatable in relation to the closure of the structure, between (i) a first position in which there is fluid communication between and through the channel and (ii) a second position in which the structure and the closure engage to inhibit fluid flow through the housing,
wherein the closure is disposed on the supporting element to enable fluid flow therearound in the first position.

20. An apparatus according to claim 19, wherein the supporting element spans an interior of the housing.

21. An apparatus according to claim 19, wherein the supporting element is substantially parallel to the filter.

22. An apparatus according to claim 19, wherein the supporting element attaches at its perimeter to the housing.

* * * * *